(12) United States Patent
Kärki et al.

(10) Patent No.: US 6,703,618 B2
(45) Date of Patent: Mar. 9, 2004

(54) METHOD AND MEASUREMENT DEVICE FOR MEASURING SUSPENSION

(75) Inventors: Pasi Kärki, Kajaani (FI); Antti Kemppainen, Oulu (FI); Arvo Rahikkala, Kajaani (FI)

(73) Assignee: Metso Automation Oy, Helsinki (FI)

( * ) Notice: Subject to any disclaimer, the term of this patent is extended or adjusted under 35 U.S.C. 154(b) by 0 days.

(21) Appl. No.: 10/190,988

(22) Filed: Jul. 8, 2002

(65) Prior Publication Data

US 2003/0030005 A1 Feb. 13, 2003

Related U.S. Application Data

(63) Continuation of application No. PCT/FI01/00046, filed on Jan. 19, 2001.

(30) Foreign Application Priority Data

Jan. 21, 2000 (FI) .............................................. 20000126

(51) Int. Cl.$^7$ ............................................... G01N 21/85
(52) U.S. Cl. ....................... 250/373; 250/574; 356/338
(58) Field of Search ................................. 250/373, 574, 250/341.5, 341.8, 354.1; 356/338, 343, 342, 328

(56) References Cited

U.S. PATENT DOCUMENTS

| | | | | |
|---|---|---|---|---|
| 4,507,556 A | * | 3/1985 | Brenholdt | ................ 250/341.5 |
| 4,838,692 A | * | 6/1989 | Brenholdt | ................ 356/343 |
| 4,971,441 A | | 11/1990 | Damlin et al. | |
| 5,416,577 A | * | 5/1995 | Haggerty et al. | ........... 356/300 |
| 5,420,682 A | | 5/1995 | Haggerty et al. | |
| 5,786,894 A | * | 7/1998 | Shields et al. | .............. 356/338 |
| 5,834,301 A | * | 11/1998 | Jeffries et al. | .............. 435/278 |
| 2001/0017195 A1 | * | 8/2001 | Trung et al. | ................... 162/49 |

FOREIGN PATENT DOCUMENTS

WO     WO-99/39044     8/1999

* cited by examiner

*Primary Examiner*—Constantine Hannaher
*Assistant Examiner*—Otilia Gabor
(74) *Attorney, Agent, or Firm*—Alston & Bird LLP

(57) ABSTRACT

The invention relates to a method and a measurement device for measuring a suspension which contains wood fibers, the method comprising directing optical radiation at pulp and measuring optical radiation emitted by the pulp. The solution comprises measuring at least one of the following two properties; kappa number and brightness. The solution comprises changing the pulp consistency in a desired range of consistency extending from a desired initial consistency to a desired final consistency. The pulp consistency and the strength of a desired wavelength from the optical radiation are measured in the desired consistency range. Measurement points are modeled with a function of the desired type by fitting the parameters of the function according to the measurement points. Finally at least one of the following two properties of the pulp is determined by means of the modeling function; kappa number and brightness.

18 Claims, 3 Drawing Sheets

| S | P | Sk1 | Pk1 | Sk2 | Pk2 |
|---|---|---|---|---|---|
| x1 | y1 | | | | |
| x2 | y2 | | | | |
| x3 | y3 | X1 | Y1 | | |
| x4 | y4 | | | | |
| x5 | y5 | | | | |
| x6 | y6 | | | | |
| x7 | y7 | | | | |
| x8 | y8 | X2 | Y2 | S1 | P1 |
| x9 | y9 | | | | |
| x10 | y10 | | | | |
| . | . | . | . | | |
| . | . | . | . | | |
| . | . | . | . | | |
| x50 | y50 | X10 | Y10 | | |
| . | . | . | . | | |
| . | . | . | . | | |
| . | . | . | . | | |

…

METHOD AND MEASUREMENT DEVICE FOR MEASURING SUSPENSION

CROSS-REFERENCE TO RELATED APPLICATIONS

This application is a Continuation of International Application PCT/FI01/00046 filed on Jan. 19, 2001, which designated the U.S. and was published under PCT Article 21(2) in English, and which is hereby incorporated herein in its entirety by reference.

BACKGROUND OF THE INVENTION

1) Field of the Invention

The invention relates to measurement of a wood fiber suspension, and particularly to optical measurement of kappa number and brightness.

2) Description of Related Art

The purpose of paper and pulp measurements is to ensure an end product of good quality. In the pulp industry, measurement of the pulp lignin content is one of the most important basic variables of pulp quality. The lignin content can be measured in the laboratory gravimetrically by hydrolyzing carbon hydrates with an acid, or using a 'kappa number'. In the standard the kappa number is defined as the amount of potassium permanganate solution with a concentration of 20 mmol/l in milliliters which one gram of dry pulp consumes in the conditions defined in the standard. This measurement is defined in greater detail in standard SCAN-C 1:77, which is incorporated herein by reference. The lignin content is about 0.15 to 0.2 times the kappa number, depending on the pulp. In the manufacture of pulp it is important to obtain real-time information on the different process stages, which enables quick control of the process. So fast measurement and control of the process cannot, however, be implemented by means of the laboratory measurement of kappa number.

Instead of laboratory measurements, it is nowadays common to use optical on-line kappa analyzers which measure lignin by means of ultraviolet radiation. In general, the measurement is based on the Lambert-Beer Law, i.e. the measurement is performed by measuring absorbance A of the suspension by means of consistency c, the distance L traveled by radiation in the suspension and an absorption constant. Mathematically the absorbance A can be expressed as follows $A=c*L*\alpha$. In other words, the measurement determines absorption of ultraviolet radiation from a pulp with a desired consistency. One particular problem related to such optical measurement is that the accuracy of the lignin content measurement depends on the relative number of fibers, which is expressed as the consistency c. It is difficult to set the consistency to a certain value as well as to measure it accurately because the consistency fluctuates in the fiber suspension measurement. This leads to an inaccurate measurement result of the kappa number.

The brightness of pulp or paper is often measured by means of the ISO brightness. This measurement is explained more closely in standard SCAN-P 3:93, which is incorporated herein by reference. In the laboratory measurement of brightness defined in the standard the brightness is determined from a dry pulp sheet. The measurement of pulp brightness is also based on the Lambert-Beer Law in the same way as the optical measurement of the kappa number, except for that the paper or pulp brightness is measured with optical radiation having a wavelength of 457 nm. The problems are similar to those related to the kappa number measurement. The measurement accuracy of brightness depends on the measurement accuracy of consistency, and since it is difficult to set the consistency to a certain value, the measurement result of brightness is inaccurate. The information provided by the brightness signal also has a certain optimum, which depends on the consistency.

BRIEF SUMMARY OF THE INVENTION

An object of the invention is to provide an improved method and an apparatus implementing the method to reduce or avoid the above-mentioned problems. This is achieved with a method of measuring a suspension which contains wood fibers, the method comprising directing optical radiation at pulp and measuring optical radiation emitted by the pulp. The method is characterized by measuring at least one of the following two properties: kappa number and brightness; and the method comprises changing the pulp consistency in a desired range of consistency extending from a desired initial consistency to a desired final consistency; measuring the pulp consistency; measuring the strength of a desired wave length from the optical radiation at different consistencies in the desired consistency range; modeling measurement points with a function of the desired type by fitting the parameters of the function according to the measurement points; and determining at least one of the following two properties of the pulp by means of the modeling function: kappa number and brightness.

The invention also relates to a measurement device for measuring a suspension which contains wood fibers, the measurement device comprising an optical power source for directing optical radiation at the suspension and at least one detector for measuring optical radiation emitted by the suspension. The measurement device according to the invention is characterized in that the measurement device is arranged to measure at least one of the following two properties: kappa number and brightness; and the measurement device is arranged to change the pulp consistency in a desired range of consistency extending from a desired initial consistency to a desired final consistency; and the measurement device is arranged to measure the pulp consistency; measure the strength of a desired wave length from the optical radiation at different consistencies in the desired consistency range; model measurement points with a function of the desired type by fitting the parameters of the function according to the measurement points; and determine at least one of the following two properties of the pulp by means of the modeling function: kappa number and brightness.

The preferred embodiments of the invention are disclosed in the dependent claims.

The invention is based on changing the suspension consistency and on continuous and simultaneous measurement of the strength of optical radiation, which provides a set of measurement points for the strength of optical radiation in the desired consistency range. A continuous function is fitted to the set of measurement points, which provides continuous dependency between the consistency and the strength of optical radiation in the desired consistency range. Finally, the desired pulp property, such as kappa number and brightness, is determined from the behavior of the continuous function.

The method and arrangement according to the invention provide several advantages. The measurement is fast because the consistency is not set to a certain value for the measurement, but optical measurements are performed by sliding the consistency. This improves the reproducibility and accuracy of the measurement. The fact that the measurement is performed from flowing pulp also improves it.

BRIEF DESCRIPTION OF THE SEVERAL VIEWS OF THE DRAWINGS

The invention will be described in greater detail by means of preferred embodiments with reference to the accompanying drawings, in which.

DETAILED DESCRIPTION OF THE INVENTION

The solution according to the invention is particularly suitable for measuring the kappa number and brightness of a suspension which contains wood fibers, but it is by no means limited to this.

In this application 'optical radiation' means electromagnetic radiation with a wavelength of approximately 40 nm to 1 mm, and 'ultraviolet radiation' means electromagnetic radiation with a wavelength of approximately 40 nm to 400 nm.

Figure 1A:
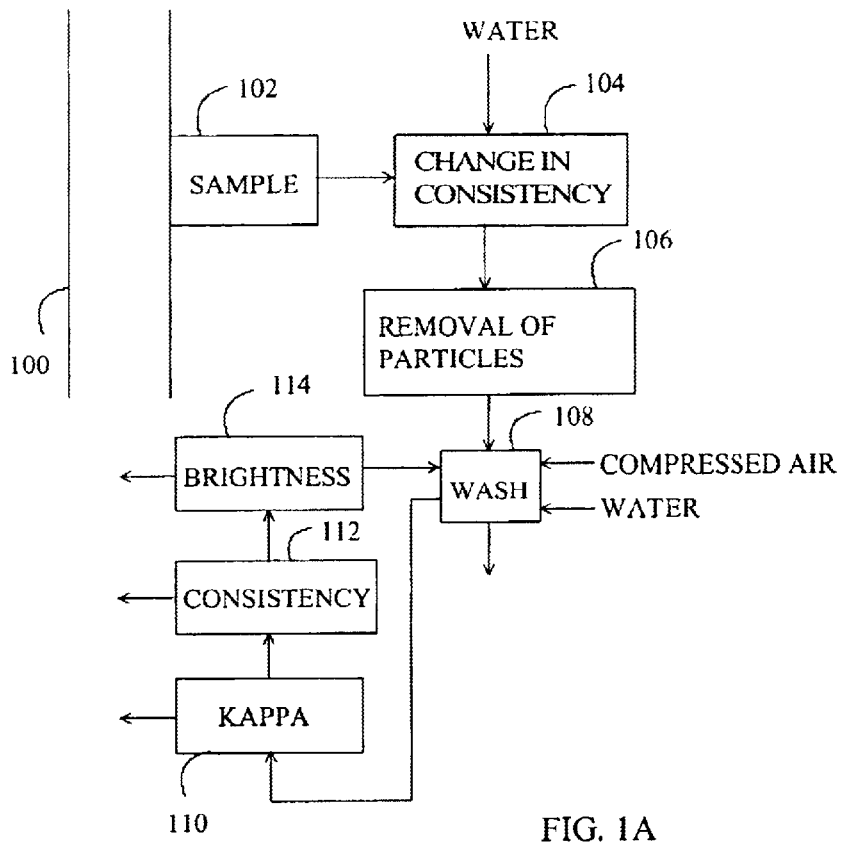
FIG. 1A is a block diagram illustrating a measurement arrangement.

First the measurement arrangement will be described with reference to FIGS. 1A and 1B, which show application of the invention in the pulp and paper industry. A sample is taken with a sampler 102 from a pipe 100, inside of which a suspension containing wood fibers, i.e. wood fiber pulp, flows. The sampler 102 may be a solution known per se, e.g. based on a piston and a cylinder. Since the pulp consistency in the pipe 100 is often too high for the measurement according to the invention (usually about 10%), the pulp consistency is decreased by adding water to the pulp in block 104, in which case the desired pulp consistency is e.g. 1%. After this, the actual sample processing is performed in block 106, where solid particles larger than fibers are removed from the sample, such as shives, chips, metal pieces, stones, etc. Samples can be taken from more than one location, and thus one sample at a time is chosen from several samples for this sample processing stage (the arrows show inputs of different samples). This is followed by washing of the sample in a washing block 108, where e.g. chemical residues and lignin dissolved in water are removed from the sample. The washed sample is circulated between the washing block 108 and measurement blocks 110, 112 and 114. Optical measurement of the kappa number is performed in block 110, the consistency of the sample is measured in block 112, and the brightness of the sample is measured optically in block 114. The solution according to the invention always includes the consistency measurement block 112. Furthermore, either one of measurement blocks 110 and 114, i.e. either the measurement block 110 for kappa number or the measurement block 114 for brightness or both are always involved in the solution according to the invention. During the measurement the pressure is increased with compressed air so high that air bubbles in the sample dissolve in water.

Figure 1B:
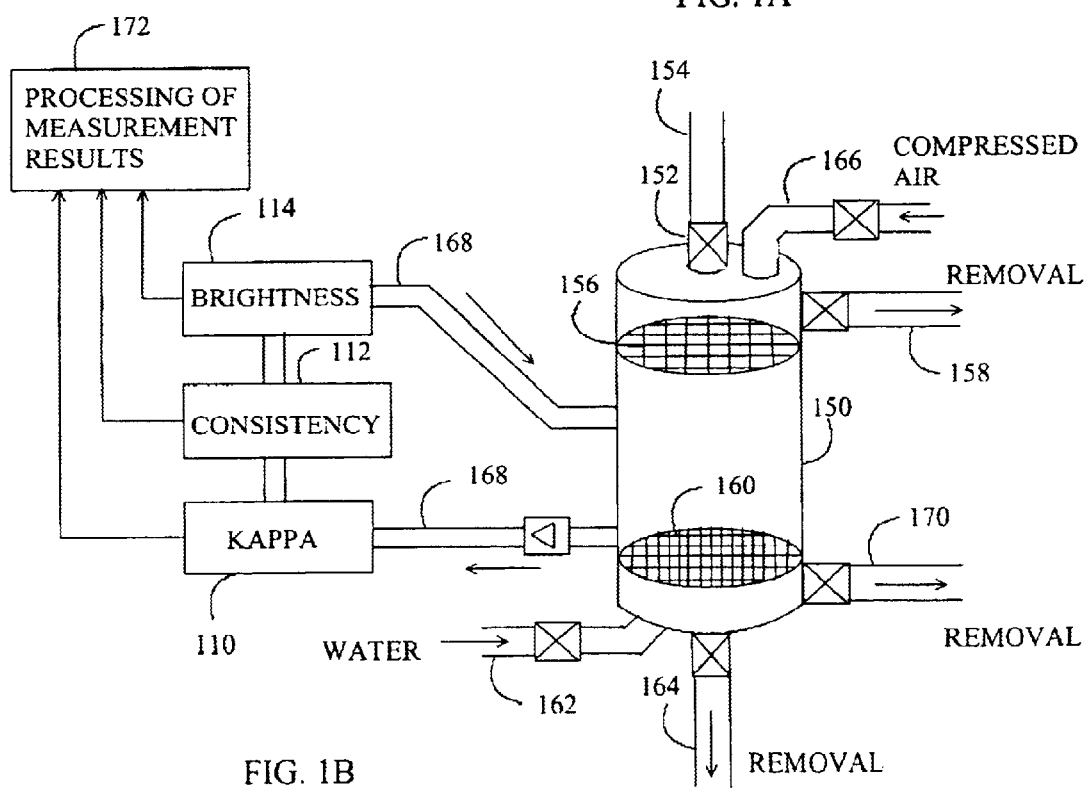
FIG. 1B illustrates a measurement arrangement.

FIG. 1B is a more detailed view of the washing section of the wood fiber suspension, but its structure as such is not relevant to the invention. The sample enters the washing section from a pipe 154 via a valve 152. Large solid particles are removed from the sample by a screen or a wire 156 and sucked into an exhaust pipe 158. The actual sample travels to a filter 160, which is so dense that it does not let the fibers of the sample through to the wire 160. The sample is washed by directing a pressurized water spray at the sample from a pipe 162. A compressed air blow can also be used for mixing the sample. Fibers that have flocculated during the washing are separated from one another. During the washing, chemical residues and substances dissolved in water can exit through the wire 160 and via a pipe 164. For performing the measurement, the washing and measuring sections 150, 110 to 114 are pressurized with compressed air. The sample to be measured is circulated in a pipe 168. The kappa number and/or the brightness are measured several times from the sample, and as the sample circulates, its consistency is changed by adding or removing water. After the measurement has been performed, the sample is removed through an exhaust pipe 170. The information collected by the measurement blocks 110 to 114 are transferred into a processing block 172 for measurement results, in which the measurements results are processed according to the method of the invention. The functions of the processing block 172 for measurement results are connected to an automatic process control computer used in the manufacture of pulp.

The features of the inventive method will be described with reference to FIGS. 1A, 1B and 2A. Optical radiation is directed at the pulp to be measured and the strength of optical radiation emitted by the pulp is measured. The method of the invention employs optical radiation for measuring at least one of the following two properties; kappa number and brightness. Brightness is preferably measured as the ISO brightness. By means of the solution according to the invention, the kappa number can be measured at least between 2 and 130, and 1 brightness at least between 30 and 95. In the method the pulp to be measured is circulated in a pipe 168 through the measurement blocks 110 to 114, in which the kappa number and the brightness are measured in addition to the consistency. During circulation the pulp consistency is changed, and the measurement of the kappa number and brightness is started when the consistency measured in block 112 is at a desired initial value SA. The measurement of the kappa number and brightness continues until the consistency measured in block 112 reaches a desired final value SL. The pulp consistency is changed so that it continuously goes through all consistencies in the desired consistency range. The consistency is changed by adding or removing water. Water can be added or removed as a constant flow. The measurement can be performed e.g. by setting the consistency to the initial value SA=0.7% and by reducing the consistency to the final value SL=0.3% by adding water. The measurement range can also differ from this, provided that the final consistency is so high that the effect of the suspension compared to pure water is clear, and the initial consistency has to be so low that the suspension emits a measurable amount of optical radiation towards the detector. The consistency range of the measurement thus extends from the desired initial value SA of consistency to the desired final value SL of consistency. To measure both the kappa number and the brightness, the strength of optical radiation is measured continuously at the desired wavelength at the consistencies of the desired consistency range.

Figures 2A, 2B:
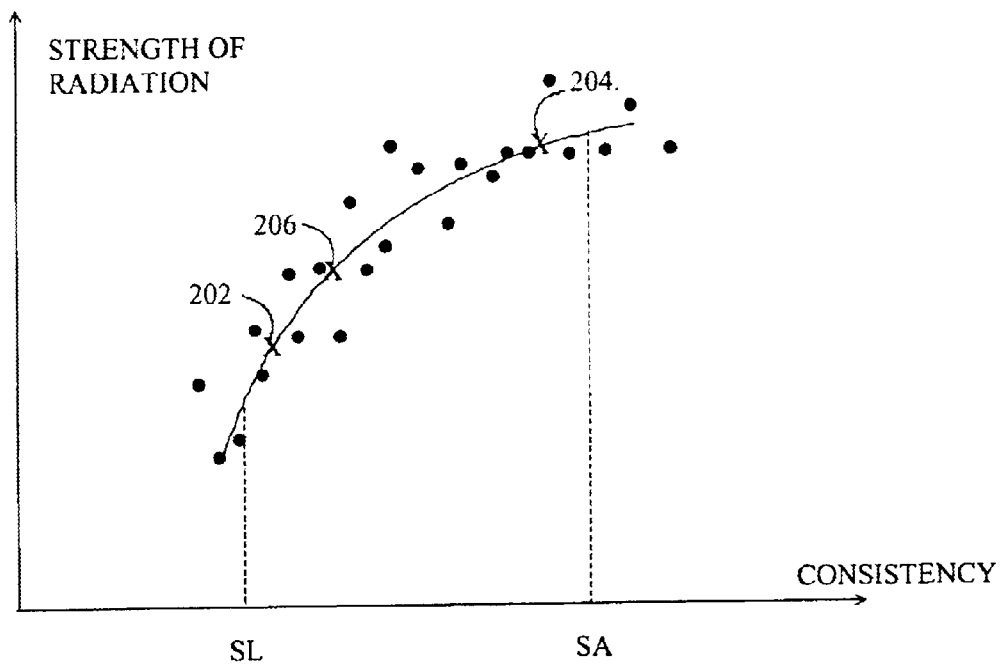
FIG. 2A illustrates measurement results and a fitted function.
FIG. 2B illustrates forming of measurement points.

In FIG. 2A each measurement point has been formed e.g. according to the table shown in FIG. 2B. Column S represents the consistency, column P the measured strength of radiation, Sk1 the averaged consistency, Pk1 the averaged strength of radiation, Sk2 the average of the averaged consistencies Sk1, Pk2 the average of the averaged strengths Pk1 of radiation. At first, five values of the measured consistency (e.g. x1 to x5) and five values of the strength of optical radiation (e.g. y1 to y5) are averaged. After this, ten averaged results (e.g. X1 to X10 and Y1 to Y10) are further averaged to obtain a value of consistency and a value of the strength of optical radiation for one measurement point (e.g. (S1, P1)) shown in FIG. 2A. The next point (S2, P2) is formed from the results X2 to X11 and Y2 to Y11, i.e. the measurement results are formed as a sliding average. If the consistency is changed by adding water as a consistent flow, the real consistency changes even during the forming of one measurement point.

The measurement points formed are modeled with a function 200 of the desired type, in which case the measurement points are fitted to this function 200. Fitting can be performed in a manner known per se, e.g. by using the least squares fitting. If the correlation of the fitted function with the measurement points is below a predetermined threshold value (i.e. the square of the difference between the function values and the measurement points is too high), the measurement is interpreted as incorrect and rejected. The desired function 200 may be an elementary function or a higher order function. Polynomial functions, for example, are suitable as functions of the desired type, in particular the second order polynomial function. In the inventive solution, the polynomial function is fitted to the measurement points, which provides a continuous function from the consistency to the strength of optical radiation, i.e. $P = f(S) = aS^2 + bS + c$, where P is the strength of optical radiation, S is the consistency, f(S) is the desired function of consistency, a is the coefficient of the second order, b is the coefficient of the first order and c is the constant term. In fitting the coefficients a, b and c are selected so that the function best describes the behavior of the measured set of points as the function of consistency. After the suitable function has been modeled, the kappa number and/or brightness are determined from the pulp on the basis of the modeled function.

In the following, the determination of the kappa number will be described more closely. According to the invention, in the determination of the kappa number two measurement points 202 and 204 are preferably chosen from the continuous function formed. The measurement points are used for calculating the kappa number K, i.e. $K = O_K$(value 202, value 204), where $O_K$ is an operation which maps the measurement points to the kappa number. The operation $O_K$ produces a result from two measurement points which is in linear relation to the kappa number. This result is then mapped to the actual kappa number by the operation $O_{K'}$. The operation $O_K$ is based on the theory of scattering and experience. According to the invention, in the measurement of brightness only one measurement point 206 from which the brightness is calculated, i.e. $B = O_B$(value 206), is preferably selected. The operation $O_B$ maps the measurement point to brightness by means of linear dependency. The operations $O_K$ and $O_B$ are selected by means of calibration measurements, in which pulp with known properties is measured.

Figure 3:
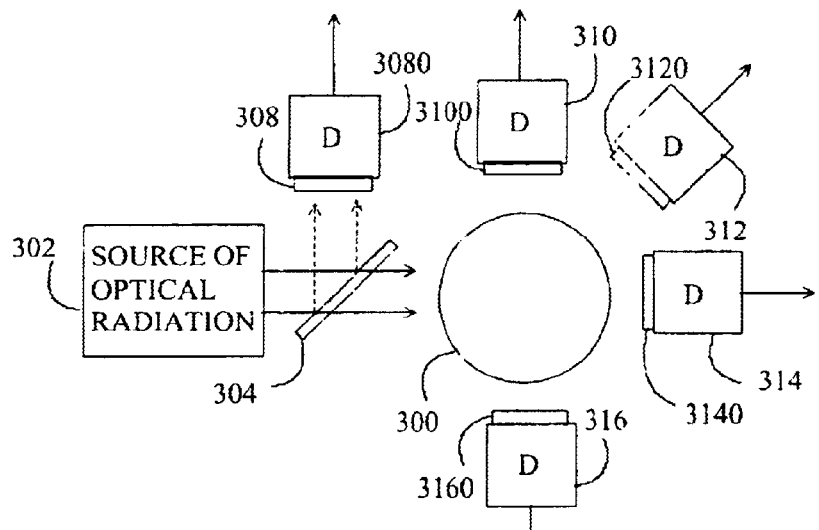
FIG. 3 illustrates optical measurement of kappa number.

The optical measurement arrangement according to the invention will be described more closely particularly in respect of the measurement of the kappa number by means of FIG. 3. In the measurement arrangement the pulp to be measured flows in the vertical direction in a measurement cell 300, which is round in the solution shown in the figure; however, the shape of the measurement cell is irrelevant to the invention. Neither are the dimensions of the measurement cell relevant to the invention. However, the larger the diameter of the measurement cell, the greater the optical power needed in the measurement is because scattering and absorption decrease the optical power that arrives at the detector. On the other hand, the thinner the measurement cell, the less the pulp to be measured affects the optical radiation. Thus the diameter of the measurement cell is optimized according to the substance to be measured. The kappa number is usually measured in the ultraviolet light, for which reason the source 302 of optical radiation has to emit at least ultraviolet light. The source 302 of optical radiation may be a Xenon lamp, for example. According to the invention, the radiation source 302 does not preferably illuminate the measurement cell continuously, but the radiation source 302 is pulsed. To measure the pulp, the measurement cell is shot with optical power pulses. The optical radiation is preferably collimated in the radiation source 302. The collimated radiation hits a semi-reflective mirror 304 provided for reference measurement. From the reflective mirror 304 the optical radiation is reflected to a reference detector 308. The reference detector 308 preferably comprises an optical filter 3080, which lets only the desired ultraviolet radiation onto the detecting surface of the detector. The reference detector 308 is used for monitoring changes in the optical power of the source 302 of optical radiation so that changes in the radiation power caused by the optical radiation source 302 would not be interpreted as changes of the kappa number. The collimated optical radiation is further directed at the measurement cell 300 and at the pulp flowing inside the measurement cell. The optical radiation scatters and absorbs into the pulp. Detectors 310, 312, 314 and 316 are preferably provided on the different sides of the measurement cell for measuring optical radiation that has scattered from the pulp and optical radiation that has passed through the pulp without scattering. Each detector 310, 312, 314 and 316 comprises an optical filter 3100, 3120, 3140 and 3160 which lets the desired ultraviolet light through.

The detector 314 is used for measuring a 'water equivalent'. This means that pure water is supplied into the measurement cell 300 and the effect of the pure water and the measurement cell 300 on the measurement is measured (e.g. effect of scattering caused by dirtying, absorption, etc.) This information can be used for correcting and specifying the kappa measurement. The detector 312 and 314 can also be used for measuring a high kappa number. The filters in the front of different detectors may let a wavelength band with the same or a different average wavelength onto the detecting surface of the detector. Three different wavelengths, for example, can be employed in the solution according to the invention. In that case the high kappa number is measured e.g. with a long wavelength and the small kappa number with a short wavelength. The kappa number between these two numbers is measured with the wavelength between the short and the long wavelength. In the solution according to the invention the wavelength of the ultraviolet radiation to be used is selected preferably from among a range of 200 nm to 400 nm. Typical wavelengths of ultraviolet light that are used for measuring the kappa number are 205 nm and 280 nm, but the invention is not limited to these values. The kappa number can also be measured using other wavelengths of optical radiation, such as IR radiation.

The solution of the invention can be used so that test measurements are performed on the pulp to be measured with all detectors 310 to 316. Since the kappa number does not usually change much in the process, unless the pulp quality is changed, only one detector can be used in the actual kappa number measurements after the test measurements. The detector whose measurements indicate best the kappa number of the process stage concerned is chosen as the detector to be used.

Figure 4:
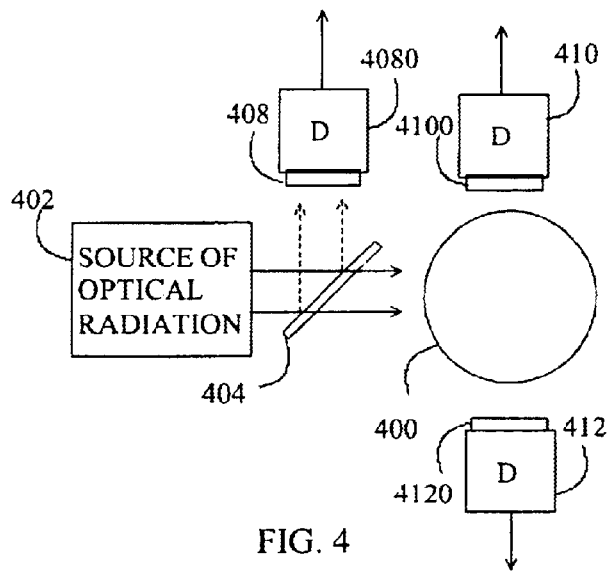
FIG. 4 illustrates optical measurement of brightness.

The measurement of brightness will be described in greater detail with reference to FIG. 4. The measurement of brightness is rather similar to that of the kappa number. An optical power source 402, which is preferably a Xenon lamp in this case, too, emits unidirectional and preferably pulsed radiation towards a measurement cell 400. Before the measurement cell 400, reference power is measured from the optical radiation using a semi-reflective mirror 404 and a detector 408, which comprises an optical filter 4080 which lets the desired wavelength at the desired optical band to the detector. Detectors 410 and 412 measure the radiation emitted by the pulp to be measured in the measurement cell 400 to determine the brightness and comprise optical filters 4100 and 4120. The filters 4100 and 4120 are selected so that brightness can be measured according to the standardized ISO brightness preferably at a wavelength of 457 nm. The detector 410 is used for measuring the water equivalent. This means that pure water is supplied into the measurement cell 400, preferably deionized water, and the effect of the pure water and the measurement cell 400 on the measurements is measured (e.g. effect of scattering caused by dirtying, absorption, etc.). This information can be used for correcting and specifying the brightness measurements.

Figure 5:
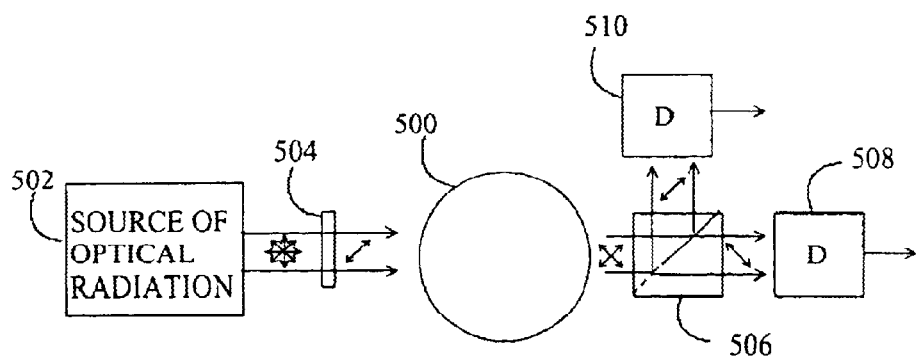
FIG. 5 illustrates measurement of consistency.

FIG. 5 illustrates one way of measuring consistency. This measurement is known per se. An optical radiation source 502 emits radiation towards a measurement cell 500. Before the measurement cell 500, the optical radiation is polarized with a polarizer 504. The pulp in the measurement cell 500 mixes polarization, and as the optical radiation exits the measurement cell, it is divided into two parts with a polarizing beam splitter 506. In that case the detector 508 receives radiation which is polarized only in one direction, and the detector 510 receives only radiation the polarization of which is orthogonal to the radiation arriving at the detector 508. The pulp consistency in the measurement cell 500 can be determined in a known manner on the basis of the difference between the radiation strengths detected by the detectors 508 and 510.

In the solution according to the invention the measurement device is calibrated to function correctly by performing calibration measurements on reference pulp. Calibration is necessary before the measurement device is actually used and needs to be performed from time to time because the route of optical radiation, for example, may change or the detector responses may change in the course of time. The reference pulp is wood fiber pulp whose properties have been measured in the laboratory and stabilized with respect to time. There is reference pulp commercially available for calibration of the measurement device according to the invention, e.g. Paprican standard reference pulp 5–96 from a Canadian manufacturer.

The following tables compare the capacity of the measurement device according to the invention with laboratory measurements. The table below compares the measurement of the kappa number with laboratory measurements, which correspond to the standard measurement.

| Measurement area (as kappa units) | <2 | 2–8 | 8–20 | 20–40 | 40–60 | >60 |
|---|---|---|---|---|---|---|
| accuracy $\sigma_L$ | 0.3 + $\sigma_L$ | 0.3 + $\sigma_L$ | 0.7 + $\sigma_L$ | 1.0 + $\sigma_L$ | 1.5 + $\sigma_L$ | 2.0 + $\sigma_L$ |
| reproducibility ($\sigma$) | 0.1 | 0.1 | 0.25 | 0.5 | 1.0 | 1.2 |

The table below compares the brightness measurement with laboratory measurements, which correspond to the standard measurement.

| Measurement area % | 40–60 | 60–85 | 85–90 + |
|---|---|---|---|
| accuracy $\sigma_L$ | 1.0 + $\sigma_L$ | 0.8 + $\sigma_L$ | 0.4 + $\sigma_L$ |
| Reproducibility ($\sigma$) | 0.4 | 0.35 | 0.3 |

In the tables $\sigma_L$ is the standard laboratory error and $\sigma$ is the standard deviation. It can be seen in the tables that the solution according to the invention corresponds well to the measurements according to the standard.

Even though the invention has been described with reference to an example according to the accompanying drawings, it is by no means limited thereto, but the invention can be modified in various ways within the scope of the inventive concept disclosed in the appended claims.

That which is claimed:

1. A method of measuring a suspension which contains wood fibers, the method comprising measuring at least one of the following two properties: kappa number and brightness by:

directing optical radiation at pulp and measuring optical radiation emitted by the pulp;

changing the pulp consistency in a desired consistency range extending from a desired initial consistency to a desired final consistency;

measuring the pulp consistency while the pulp consistency is being changed;

measuring the strength of a desired wavelength from the optical radiation at different consistencies in the desired consistency range;

modeling measurement points with a function of the desired type by fitting the parameters of the function according to the measurement points; and determining at least one of the following two properties of the pulp by means of the modeling function: kappa number and brightness.

2. A method according to claim 1, further comprising measuring in the method the kappa number of pulp by determining two measurement points corresponding to the predetermined consistency by means of the modeling function, and determining the kappa number of pulp by means of the measurement points.

3. A method according to claim 1, further comprising measuring the kappa number by means of ultraviolet radiation, wherein said measuring comprises measuring values for kappa number using at least two wavelengths and determining the kappa number based on the measured values.

4. A method according to claim 1, further comprising measuring in the method the brightness of pulp by determining a measurement point corresponding to a predetermined consistency value by means of the modeling function, and determining the brightness of pulp by means of the measuring point.

5. A method according to claim 1, further comprising measuring the brightness at a wavelength band having an average wavelength of 457 nm.

6. A method according to claim 1, further comprising using the method for measuring reference pulp with predetermined properties to calibrate the measurement results.

7. A method according to claim 1, further comprising changing the pulp consistency so that the pulp consistency continuously goes through all consistencies in the desired consistency range.

8. A method according to claim 1, further comprising modeling the measurement points with a continuous function.

9. A method according to claim 1, further comprising modeling the measurement points with a second order polynomial function.

10. A measurement device for measuring a suspension which contains wood fibers, the measurement device comprising:

an optical power source for directing optical radiation at the suspension; and at least one detector for measuring optical radiation emitted by the suspension, wherein the measurement device is arranged to measure at least one of the following two properties: kappa number and brightness, and the measurement device is arranged to:

change the pulp consistency in a desired consistency range extending from a desired initial consistency to a desired final consistency:

measure the pulp consistency;

measure the strength of a desired wavelength from the optical radiation at different consistencies in the desired consistency range;

model measurement points with a function of the desired type by fitting the parameters of the function according to the measurement points; and determine at least one of the following two properties of the pulp by means of the modeling function: kappa number and brightness.

11. A measurement device according to claim 10, wherein to measure the kappa number, the measurement device is arranged to determine two measurement points corresponding to the predetermined consistency by means of the modeling function, and determine the kappa number of pulp by means of the measurement points.

12. A measurement device according to claim 10, wherein the measurement device is arranged to measure the kappa number by means of ultraviolet radiation.

13. A measurement device according to claim 10, wherein to measure the brightness, the measurement device is arranged to determine a measurement point corresponding to a predetermined consistency value by means of the modeling function, and determine the brightness of pulp by means of the measuring point.

14. A measurement device according to claim 10, wherein the measurement device is arranged to measure the brightness at a wavelength band having an average wavelength of 457 nm.

15. A measurement device according to claim 10, wherein the measurement device is arranged to measure reference pulp with predetermined properties to calibrate the measurement results.

16. A measurement device according to claim 10, wherein the measurement device is arranged to change the pulp consistency so that the pulp consistency continuously goes through all consistencies in the desired consistency range.

17. A measurement device according to claim 10, wherein the measurement device is arranged to model measurement points with a continuous function.

18. A measurement device according to claim 10, wherein the measurement device is arranged to model measurement points with a second order polynomial function.

* * * * *